United States Patent [19]

Horrobin

[11] Patent Number: 5,516,800
[45] Date of Patent: May 14, 1996

[54] SCHIZOPHRENIA

[75] Inventor: David F. Horrobin, Guildford, England

[73] Assignee: Scotia Holdings PLC, England

[21] Appl. No.: 154,481

[22] Filed: Nov. 19, 1993

[30] Foreign Application Priority Data

Nov. 26, 1992 [GB] United Kingdom .................. 9224809

[51] Int. Cl.$^6$ ..................................................... A61K 31/20
[52] U.S. Cl. ......................................................... 514/560
[58] Field of Search ................................... 514/558, 560

[56] References Cited

U.S. PATENT DOCUMENTS

| | | | |
|---|---|---|---|
| 4,526,902 | 7/1985 | Rubin | 514/560 |
| 4,588,721 | 5/1986 | Mahan | 514/220 |
| 4,882,345 | 11/1989 | Gueremy et al. | 514/367 |
| 4,882,352 | 11/1989 | Horn | 514/438 |
| 4,977,187 | 12/1990 | Horrobin | 514/560 |
| 5,070,101 | 12/1991 | Kaminski | 514/399 |
| 5,151,419 | 9/1992 | Perenyi et al. | 514/226.2 |

FOREIGN PATENT DOCUMENTS

| | | |
|---|---|---|
| 0296751 | 12/1988 | European Pat. Off. . |
| 0298644 | 1/1989 | European Pat. Off. . |
| 0347056 | 12/1989 | European Pat. Off. . |
| 0454102 | 10/1991 | European Pat. Off. . |

OTHER PUBLICATIONS

Neuroscience and Biobehavioral Reviews vol. 16, pp. 193–205, 1992 Wainwright "Do Essential Fatty Acids Play a Role in Brain and Behavioral Development?".

Biochemical Pharmacology, vol. 44, No. 2, pp. 317–323, 1992 Fischer et al "Schizophrenic Patients Treated with High Dose Phenothiazine or Thioxanthene Become Deficient in Polyunsaturated Fatty Acids in Their Thrombocytes".

Stedman's Medical Dictionary, 25th Edition, p. 1390, 1989.

Van Kammen et al, Medline Abstract #89372545 of Ann. N.Y. Acad. Sci, 1989, 559 (411–23), Polyunsaturated Fatty Acids, Prostaglandins, and Schizophrenia.

Maruha, K. K., WPIDS Abstract #94–128761 of JP06072864, 1984, Antipsychotic Agents–Contain Doca Sahexamenoic Acid.

Lehninger Albert, Biochemistry Second Edition, 1975, pp. 281–282.

*Primary Examiner*—Richard L. Raymond
*Assistant Examiner*—Deborah Lambkin
*Attorney, Agent, or Firm*—Nixon & Vanderhye

[57] ABSTRACT

The negative symptoms of schizophrenia and/or low cell membrane levels of EFAs may be treated with a combination of arachidonic acid and docosahexaenoic acid.

8 Claims, No Drawings

SCHIZOPHRENIA

Essential fatty acids (EFAs) are essential constituents of all cell membranes including those in the brain. There are two series of EFAs, the n-6 derived from linoleic acid and the n-3 derived from alpha-linolenic acid. Their metabolic pathways are shown in Table 1.

TABLE 1

| n-6 | n-3 |
|---|---|
| 18:2 delta-9,12 (linoleic acid) | 18:3 delta-9,12,15 (alpha-linolenic acid) |
| delta-6 desaturase ↓ | |
| 18:3 delta-6,9,12 (gamma-linolenic acid) | 18:4 delta-6,9,12,15 (stearidonic acid) |
| elongation ↓ | |
| 20:3 delta-8, 11,14 (dihomo-gamma-linolenic acid) | 20:4 delta-8,11,14,17 |
| delta-5 desaturase ↓ | |
| 20:4 delta-5,8,11,14 (arachidonic acid) | 20:5 delta-5,8,11,14,17 ('eicosapentaenoic acid') |
| elongation ↓ | |
| 22:4 delta-7,10,13,16 (adrenic acid) | 22:5 delta-7,10,13,16,19 |
| delta-4 desaturase ↓ | |
| 22:5 delta-4,7,10,13,16 | 22:6 delta-4,7,10,13,16,19 ('docosahexaenoic acid') |

Whereas in most cell membranes linoleic acid is an important component, this is not true of the brain. In the brain the two most important EFAs by concentration are arachidonic acid (AA) and docosahexaenoic acid (DHA). Dihomo-gamma-linolenic acid (DGLA) and eicosapentaenoic acid (EPA) are also important in the brain, but are present in much lower concentrations than AA and DHA. The other fatty acids of the n-3 and n-6 series are minor components but could nevertheless play important functional roles.

Schizophrenia is a common and serious psychiatric disorder affecting about 1% of the population. It is diagnosed according to criteria set out in Diagnostic Standards and Methods III—Revised (DSM III R), a manual developed by the American Psychiatric Association and accepted in most countries. Patients classified as schizophrenic under DSM III R may show a wide variety of signs and symptoms. There is discussion as to whether there are two or three separate sub-groups of patients within the overall DSM III R classification. Two of these sub-groups in particular, those with so-called "negative" and those with so-called "positive" symptoms have been much discussed. In the negative groups features of apathy, social withdrawal and a low level or absence of other symptoms predominate. The negative group may be clearly identified by using the negative component scores of standard psychiatric rating scales such as the Brief Psychiatric Rating Scale (BPRS) or by rating scales specifically designed to identify patients with the negative schizophrenia syndrome (sometimes also called the deficit syndrome). One very widely used negative scale is that devised by Andreasen et al. in Arch. Gen. Psychiatry (1982) Volume 39, pages 789–794, although others are available.

We have been interested for a number of years in the possibility that membrane abnormalities, particularly in the brain but also in other tissues, may play a role in schizophrenia. We have therefore performed analyses of the EFA levels in plasma and red blood cell phospholipids on various groups of schizophrenics and have compared those levels to those in normal individuals.

In plasma (FIG. 1), all the EFAs showed a broadly unimodal distribution in both normal and schizophrenic individuals. Mean figures were different from normal in the schizophrenic patients, sometimes significantly so, and the scatter of values was often greater in the schizophrenics but there was no evidence of more than one schizophrenic population.

In the red blood cells (FIG. 2) much the same was true for most of the fatty acids such as linoleic acid. Again distribution curves were often irregular in the schizophrenics as compared to the regular curves seen in the normals but for most fatty acids there was no clear evidence of more than one population. This was not true, however, of the two fatty acids particularly important in the brain, AA (20:4 n-6), and DHA (22:6 n-3), and of the other two fatty acids of lesser importance in the brain, EPA (20:5 n-3) and DGLA (20:3 n-6). For these fatty acids concentrations in red cell membranes showed a clear biphasic distribution of the kind illustrated for AA and DHA in FIGS. 1 and 2. Further, one group of patients had values grouped around the normal region but another group of patients had a clearly different distribution with levels of the four fatty acids much lower than in normals or in other schizophrenics. These abnormal values appear related to the occurrence of symptoms generally regarded as being of the negative type.

This was confirmed in a study in which 13 patients with persistent negative schizophrenic symptoms were compared with 12 patients with persistent positive symptoms and 8 unequivocally normal individuals. In plasma, AA and DHA levels were relatively similar in all three groups. In contrast, in red cells, whereas the phospholipid DHA and AA levels were near normal in the positive schizophrenics, in the negative group they were highly significantly below normal ($p<0.001$ in each case). In the table below the figures are means±SD. All figures are in mg/100 mg phospholipid

| Red cell fatty acid | Normal (n = 8) | Positive schizo (n = 12) | Negative schizo (n = 13) |
|---|---|---|---|
| AA | 16.8 ± 0.5 | 15.5 ± 3.5 | 7.4 ± 2.3 |
| DHA | 5.1 ± 0.2 | 5.9 ± 1.8 | 2.2 ± 1.8 |

It appears therefore that around half of all patients currently classified as schizophrenic have a clear abnormality of EFA metabolism. These patients are those who exhibit the negative symptoms of the disease. Since plasma EFA levels are not far from normal, this group of patients clearly cannot incorporate the four major EFAs with 20 and 22-carbon atoms, namely AA, DHA, EPA and DGLA, into the red cell membranes normally. It is to be expected that the other, minor 20 and 22 carbon fatty acids show the same defect. It is also to be expected that this abnormality will be apparent in membranes throughout the body, particularly those of the brain. For fatty acids other than linoleic acid, there is a strong positive correlation between red cell and brain levels. This has been shown specifically for DHA by Connor in FASEB J, (1993) Volume 7, A152. Therefore, since neuronal membranes are critical for normal brain function, it is likely that these abnormalities are a cause of the negative schizophrenic symptoms in these patient groups.

The red cell membranes in the patient groups with low 20 and 22-carbon fatty acids do contain some of these fatty acids. The mechanism for incorporation is therefore slow rather than absent. For this reason it will be possible to increase the amounts of the AA and DHA in cell membranes in schizophrenics by supplying additional amounts of these fatty acids.

The present invention is therefore in one aspect to treat the negative syndrome of schizophrenia and/or low cell membrane levels of $C_{20}$ or $C_{22}$ EFAs, by administering a combination of AA and DHA. It is preferred that the ratio of AA to DHA varies within the range of 20:1 to 1:20 preferably 5:1 to 1:5, and very preferably 3:1 to 1:3. Other EFAs such as EPA and DGLA may optionally be present. The EFAs may be administered in any appropriate form at a daily dose of from 10 mg to 20 g/day for each EFA, preferably 100 mg to 10 g/day, very preferably 200 mg to 3 g/day. Since gamma-linolenic acid (GLA) is rapidly converted to DGLA, it may replace DGLA in whole or in part in the formulation.

By the negative syndrome of schizophrenia herein is meant patients displaying at least one negative characteristic, identifiable by the rating scales described herein.

Another aspect of the invention is to treat all cell membrane abnormalities lying in low DHA and AA levels as above, by administering such EFA combinations.

A further aspect of the invention lies in the use of a combination of AA and DHA in the preparation of a medicament for the treatment of the negative syndrome of schizophrenia and all cell membrane abnormalities as above.

The forms in which the fatty acids may be presented include any form which will allow the assimilation of the fatty acids into the body and into red cell membranes as indicated by a change in the composition of these red cell membranes on administration of the fatty acid. Suitable forms may be free fatty acids, physiologically acceptable esters of any type, mono-, di and triglycerides, amides, salts including sodium, potassium, lithium, calcium, zinc and other salts, and phospholipids including phosphatidyl (P)-choline, P-serine, P-inositol and P-ethanolamine and any other appropriate form. Routes of administration may include oral, enteral, parenteral (including subcutaneous, intramuscular, intravenous and intraperitoneal), topical, rectal, vaginal or by any other appropriate route.

As noted above, the schizophrenics with low red cell 20 and 22-carbon EFA levels appear on clinical examination to fall into the group with predominantly negative features. Some schizophrenics have both negative and positive features and it is not always possible to distinguish the group on clinical grounds. While, therefore, the treatment is particularly applicable to patients with any of the negative features of the disease, it can be applied to all schizophrenics in the knowledge that some will respond, while others who do not respond are most unlikely to be harmed, the fatty acids concerned being normal dietary components and bodily constituents. This, of course, is characteristic of the treatment of most diseases, where only some patients will respond to any particular measure.

The invention is further illustrated by the following Examples.

EXAMPLES

1. A triglyceride or a mix of triglycerides containing AA and DHA in a ratio ranging from 1:3 to 3:1 and formulated in a topical, oral or parenteral, rectal or vaginal dosage form such that a daily dose of between 20 mg and 10 g of each fatty acid can be delivered effectively. Such triglycerides might be a triglyceride with 2 molecules of DHA and one of AA, with 2 molecules of AA and one of DHA or with one of AA, one of DHA and one of another appropriate fatty acid formulated as 500 mg or 1 g soft gelatin capsules.

2. A mix of triglycerides as in 1, except that one triglyceride will contain 1–3 molecules of DHA and the other 1–3 molecules of AA, formulated as 500 mg soft gelatin capsules.

3. A triglyceride or mix or triglycerides as in 1 except that the fatty acids present are AA, DGLA, EPA and DHA.

4–6. As in 1–3 except that the fatty acids are present as free acids, for example a capsule containing 200 mg AA, 200 mg DHA and 200 mg other carrier fatty acids.

7–9. As 1–3 except that the fatty acids are present as salts, such as lithium salts. The lithium salts, as well as being suitable for oral formulation as capsules or tablets with appropriate carriers, are also suitable for parenteral or enteral formulation, for example Li AA and Li DHA in a 20% alcoholic solution in sterile ampoules containing 500 mg of each fatty acid for iv. administration.

10–12. As 1–3 except that the fatty acids are present as esters such as ethyl esters.

13–15. As 1–3 except that the fatty acids are present as amides.

16–18. As 1–3 except that the fatty acids are present as phospholipids such as P-choline, P-serine, P-inositol or P-ethanolamine or any other appropriate phospholipid.

I claim:

1. A method of treating negative syndrome schizophrenia in a patient identified by the presence of low levels of AA and DHA in cell membranes, by administering to said patient an effective amount of a composition consisting of arachidonic acid (AA) and docosahexaenoic acid (DHA) and a pharmacologically carrier or diluent.

2. The method according to claim 1 wherein said membranes are of red blood cells.

3. The method according to claim 1 wherein the AA and DHA are administered in a weight ratio of AA:DHA of 20:1 to 1:20.

4. The method according to claim 3 wherein the AA:DHA weight ratio is 5:1 to 1:5.

5. The method according to claim 4 wherein the AA:DHA weight ratio is 3:1 to 1:3.

6. The method according to claim 1 wherein the AA and DHA are each administered as a daily dose of between 20 mg and 10 g.

7. The method according to claim 1 wherein the AA and DHA are administered in a form selected from the group consisting of free fatty acids physiologically acceptable esters, mono-, di and triglycerides, amides, salts and phospholipids.

8. The method according to claim 1 wherein the AA and DHA are administered by a route selected from the group consisting of oral, enteral, parenteral, topical, rectal and vaginal routes.

* * * * *